(12) United States Patent
Leigh et al.

(10) Patent No.: US 8,632,832 B2
(45) Date of Patent: Jan. 21, 2014

(54) DIRECT DISSOLUTION

(75) Inventors: Steve Leigh, Muttenz (CH); Mathew Louis Steven Leigh, Muttenz (CH); Peter Van Hoogevest, Muttenz (CH)

(73) Assignee: Phares Pharmaceutical Research N.V., Curacao (NL)

( * ) Notice: Subject to any disclaimer, the term of this patent is extended or adjusted under 35 U.S.C. 154(b) by 494 days.

(21) Appl. No.: 11/984,754

(22) Filed: Nov. 21, 2007

(65) Prior Publication Data
US 2008/0311267 A1     Dec. 18, 2008

Related U.S. Application Data

(63) Continuation of application No. PCT/EP2006/004842, filed on May 22, 2006.

(30) Foreign Application Priority Data

May 23, 2005    (EP) .................................. 05011108

(51) Int. Cl.
| A23L 1/27 | (2006.01) |
| A47J 39/00 | (2006.01) |
| A23D 7/00 | (2006.01) |

(52) U.S. Cl.
USPC ........................... 426/540; 426/520; 426/601

(58) Field of Classification Search
USPC .............. 426/73, 601, 615, 540, 20
See application file for complete search history.

(56) References Cited

U.S. PATENT DOCUMENTS

| 2,756,177 A | 7/1956 | Cannalonga et al. |
| 2,861,891 A | 11/1958 | Bauernfeind et al. |
| 3,992,329 A * | 11/1976 | Eaton et al. ....................... 502/7 |
| 4,871,551 A | 10/1989 | Spencer |
| 5,364,563 A * | 11/1994 | Cathrein et al. ................ 426/73 |

(Continued)

FOREIGN PATENT DOCUMENTS

| CL | 42.063 | 8/1998 |
| CL | 42.763 | 9/1999 |

(Continued)

OTHER PUBLICATIONS

NPL: Buchwald M et al. 'Optical properties of Astaxanthin solution and aggregates' Biochemistry, vol. 7(2), p. 834-838, 1968.*

(Continued)

*Primary Examiner* — Humera Sheikh
*Assistant Examiner* — Bhaskar Mukhopadhyay
(74) *Attorney, Agent, or Firm* — Buchanan Ingersoll & Rooney PC (57) ABSTRACT

The present disclosure describes a method for the continuous dissolution of e.g. crystalline astaxanthin or canthaxanthin suspension in oil, by applying heat for a predetermined period using an in-line or optionally batch wise-process, followed by cooling the heated solution with an oil phase or heat exchanger. The resulting oil solution may be used as such or added directly to feed components which are turned into feed compositions by extrusion, compaction or granulation. Alternatively the oil solution is spray coated or directly loaded to extruded or compacted pellets and granulates. The disclosure avoids using formulated carotenoids prepared by known multi-step production methods requiring solvents, solvent removal, cooling and emulsification with an aqueous phase or precipitation and recovery steps. Thus the present invention is a more economical, efficient and environmentally friendly method to add nutrients and colorants to feed compositions instead of using colloid dispersed particulate hydrocolloid compositions.

33 Claims, 1 Drawing Sheet

(56) References Cited

U.S. PATENT DOCUMENTS

| | | | |
|---|---|---|---|
| 5,654,488 A * | 8/1997 | Krause et al. ................. 568/345 |
| 5,780,056 A * | 7/1998 | Akamatsu et al. ............ 424/464 |
| 5,863,953 A | 1/1999 | Luddecke et al. |
| 5,968,251 A * | 10/1999 | Auweter et al. ................ 426/73 |
| 6,287,615 B1 * | 9/2001 | Runge et al. ................ 426/268 |
| 6,296,877 B1 | 10/2001 | Auweter et al. |
| 6,406,735 B2 | 6/2002 | Stein et al. |
| 6,555,148 B1 | 4/2003 | Hamstra et al. |
| 6,635,293 B2 | 10/2003 | Fullmer et al. |
| 6,664,300 B2 | 12/2003 | Mori et al. |
| 6,709,688 B1 | 3/2004 | Breivik et al. |
| 6,863,914 B1 | 3/2005 | Auweter et al. |
| 7,056,525 B2 * | 6/2006 | Runge et al. ................ 424/439 |
| 2002/0099102 A1 | 7/2002 | Mori et al. |
| 2003/0129290 A1 | 7/2003 | Fullmer et al. |
| 2005/0014824 A1 | 1/2005 | Kulas et al. |
| 2005/0090469 A1 * | 4/2005 | Lockwood et al. ............ 514/59 |
| 2005/0169999 A1 | 8/2005 | Eller et al. |
| 2005/0244510 A1 * | 11/2005 | Smith .......................... 424/617 |
| 2008/0206349 A1 * | 8/2008 | Barnwell et al. .............. 424/501 |

FOREIGN PATENT DOCUMENTS

| | | | |
|---|---|---|---|
| CL | 01053-2000 | 6/2001 | |
| CL | 2520-2002 | 11/2002 | |
| EP | 0 845 503 A2 | 6/1998 | |
| EP | 0 937 412 A1 | 8/1999 | |
| EP | 1 173 521 A1 | 1/2002 | |
| EP | 1 227 082 A1 | 7/2002 | |
| EP | 1 442 083 A1 | 8/2004 | |
| JP | 2002-316924 A | 10/2002 | |
| JP | 2004-514419 A | 5/2004 | |
| JP | 2005-506841 A | 3/2005 | |
| WO | WO 96/23420 A1 | 8/1996 | |
| WO | WO 97/42838 | 11/1997 | |
| WO | WO 00/66665 A1 | 11/2000 | |
| WO | WO 01/05438 * | 1/2001 | ............ A61K 49/00 |
| WO | WO 02/08182 A1 | 1/2002 | |
| WO | WO 03/034841 A1 | 5/2003 | |
| WO | WO 03/040238 A1 | 5/2003 | |
| WO | WO 03/102116 A2 | 12/2003 | |

OTHER PUBLICATIONS

International Search Report for PCT/EP2006/004842, dated Sep. 28, 2006.

Japanese Office Action mailed on Jul. 23, 2012, in corresponding Japanese Patent Application No. 2008-512749, with English translation.

* cited by examiner

DIRECT DISSOLUTION

RELATED APPLICATION

This application claims priority under 35 U.S.C. §119 to EP Application 05011108.7 filed in Europe on May 23, 2005, and as a continuation application under 35 U.S.C. §120 to PCT/EP2006/004842 filed as an International Application on May 22, 2006, designating the U.S., the entire contents of which are hereby incorporated by reference in their entireties.

TECHNICAL FIELD

This disclosure relates to a continuous method for dissolving carotenoids in edible oils and fats. More specifically it concerns dissolving carotenoid directly in oil by heating a suspension in an oily medium followed by cooling preferably with oil at a lower temperature using an in-line process. The resulting oil solution may be used as such, or for in-line or batch-wise production of nutritional compositions comprising carotenoids.

BACKGROUND INFORMATION

Carotenoids are widely used across the pharmaceutical, neutraceutical, cosmetic, food and feed industries. The compositions are collectively referred to as nutritional compositions in this specification. In the feed industry, carotenoids have utility as colourant additive and essential nutrients. Delivering carotenoids that have good absorption and bioavailability is a major problem because the compounds are practically insoluble in water at ambient temperatures. Specific examples are astaxanthin and canthaxanthin for aquaculture and beta carotene and zeaxanthin for the poultry industry. Poor solubility is a major hurdle to good bioavailability. The crystalline forms of these carotenoids are not used as such because of poor dissolution characteristics and have therefore to be formulated first to become useful feed and nutrient additives. Particulate compositions prepared by spray drying or catch beadlet technology described in U.S. Pat. No. 2,756,177 containing astaxanthin or canthaxanthin in a polymer matrix are extensively used in feed production. The dispersible beadlets or granules are added as dry powders or they may be dissolved/dispersed in water before or after processing into feed compositions.

The present disclosure is for preparing oily carotenoid solutions by dispersing carotenoids which may be crystals, amorphous particles or aggregates and combinations thereof in oil and dissolving the carotenoid in heated oil phase followed by cooling preferably with an oil phase using a continuous in-line method. The resulting oily carotenoid composition may be used as such directly for preparing feed and other compositions. The method does not require the carotenoid to be formulated as colloid-dispersed dry powder or particulate compositions comprising hydrocolloids, thereby avoiding the high costs of solvents and the energy associated with solvent recovery and powder production. Furthermore the method does not require emulsifying the heated carotenoid solution with an excess of an aqueous phase and an emulsifier to simultaneously form an oil-in-water emulsion. Therefore, instant disclosure gives significant cost reductions in the production and supply chain particularly for feed products.

U.S. Pat. No. 5,364,563 describes a method for preparing colloid-dispersed water-dispersible, powdered carotenoid preparations. A suspension of the carotenoid comprising 10-50% by weight of the carotenoid in high-boiling point oil is brought directly into contact with super heated steam under increased pressure and temperature and immediately cooled and emulsified in an aqueous solution of a hydrocolloid followed by spraying and drying the o/w emulsion to a powder.

U.S. Pat. No. 6,296,877, describes a method of preparing water dispersible particles or beadlets which comprises dissolving at least two hydrocolloids and a carotenoid using water miscible solvents under increased pressure and temperature. The carotenoid is immediately precipitated, in a colloidally disperse form, from the molecularly disperse solution by rapidly mixing and cooling the organic solvent solution with an aqueous solution of a swellable colloid and the resulting dispersion is freed from the solvent and the dispersing medium in a conventional manner. In common with U.S. Pat. No. 5,364,563 the method requires either solvents and/or recovery steps to obtain colloid-dispersed particulate carotenoid compositions.

U.S. Pat. No. 6,664,300 relates to a process for preparing a solution of a carotenoid in a high boiling point organic liquid to produce a carotenoid emulsion by heating a suspension of the carotenoid in a high boiling organic liquid to dissolve the carotenoid, and then immediately adding the resulting solution into an aqueous solution of an emulsifier such as a hydrocolloid, to emulsify the solution. The emulsion is spray dried to recover the colloid-dispersed carotenoid powder.

All the methods described are characterised by an essential step of emulsifying the heated carotenoid solution in excess water with a hydrocolloid and/or an emulsifier. By comparison WO03/102116 describes oil dispersible carotenoid compositions comprising lipophilic polymers/dispersants that are dissolved in oil, without applying inline and defined short heating procedures, and cooling with oil prior to preparing fish feed and other compositions.

SUMMARY

The disclosure describes an in-line method and a related apparatus for carotenoid dissolution, which may be integrated in-line into continuous or batch-wise production methods for food and feed compositions. The method avoids the need to prepare and purchase separate dry powder carotenoid formulations for incorporation into feed and food compositions. Continuous preparation of oily carotenoid solutions with the desired carotenoid concentration after cooling is thus possible for processing into fish feed, starting from, e.g., unformulated carotenoids. The dissolution and cooling apparatus disclosed may also be housed in a freestanding module or linked modular units for preparing large amounts of oily carotenoid solution. The module is particularly suitable for in-line connection to (existing) feed production lines. The process can be carried out under normal atmospheric conditions. However it may also be performed under pressure if pressurised (e.g. supercritical) fluids and equipment are employed on its own or in combination with heating the oil.

According to an exemplary embodiment, the disclosure describes an in-line process for dissolving a carotenoid composition in a high boiling point oil phase at a temperature which may be up to the boiling point of the oil phase for a predetermined time in a heating zone comprising e.g. a mixing chamber followed immediately by rapidly cooling, e.g., in a second mixing chamber to prepare an oily carotenoid solution. The temperature required for dissolving the carotenoid is between the temperature of the said carotenoid suspension and the boiling point of the oil phase. The term mixing includes the addition of the heated oily solution to the cooling medium or vice versa by adding the cooling medium to the heated oily solution.

Accordingly the disclosure describes the following exemplary embodiments:

A method for preparing an oily carotenoid composition which comprises
- i) preparing a suspension by dispersing at least one carotenoid in a physiologically acceptable oil phase;
- ii) heating the suspension in-line for up to 30 s. at a temperature maximally up to the boiling point of the oil phase to dissolve the suspended carotenoid in said oil phase and obtain a heated oily carotenoid solution; and
- iii) cooling the heated oily carotenoid solution by methods selected from the group consisting of mixing with a physiological acceptable oil phase that is at a lower temperature than the heated oily solution and using a heat exchanger.

DETAILED DESCRIPTION

The disclosure further relates to the following exemplary embodiments:

A method, wherein the oily carotenoid suspension is heated at 100-230° C. for less than 5 s by mixing with an oil phase which is at a higher temperature than the said suspension and wherein the heating of the oil phase is performed by using means selected from the group consisting of a heat exchanger heated with super heated steam, a heat exchanger heated with supercritical gases, a heat exchanger heated by electricity, heat generated by rotor stator mixers and heat generated by ultra-sonic mixers.

A method, wherein the carotenoid is a crystalline carotenoid compound.

A method, wherein the heated oily carotenoid solution is cooled by applying methods selected from the group consisting of in-line addition of a physiologically acceptable oil phase which is at a lower temperature than the heated oily carotenoid solution, batch wise addition to a physiologically acceptable oil phase which is at a lower temperature than the heated oily carotenoid solution and using an in-line heat exchanger.

A method, wherein the heated and cooled oily carotenoid solution contains up to 20'000 ppm of carotenoid and wherein the cooling of the heated oily carotenoid solution is carried out in-line by the addition of fish oil.

A method, wherein the temperature of the oily carotenoid solution after cooling is below 60° C. and the cooling step is performed in a time of less than 30 s.

A method, wherein the oily carotenoid suspension comprises carotenoid particles which are substantially pure and wherein the carotenoid is selected from the group consisting of synthetic or natural astaxanthin, canthaxanthin, beta carotene and zeaxanthin and wherein 90% of said particles have a diameter less than 15 μn.

An additional exemplary embodiment of the disclosure relates to a method for preparing nutritional compositions, which comprises
- (i) preparing a suspension by dispersing at least one carotenoid in a physiologically acceptable oil;
- (ii) heating the suspension in-line for up to 30 s at a temperature maximally up to the boiling point of the oil phase to dissolve the suspended carotenoid in said oil phase and obtain a heated oily carotenoid solution;
- (iii) cooling the heated oily carotenoid solution by methods selected from the group consisting of mixing with a physiological acceptable oil phase that is at a lower temperature than the heated oily solution and using a heat exchanger.
- (iv) adding the cooled oily carotenoid solution to nutritional compositions.

A further exemplary embodiment of the disclosure relates to a method for preparing nutritional compositions, which comprises
- i) preparing a suspension by dispersing at least one carotenoid in a physiologically acceptable oil;
- ii) heating the suspension in-line for up to 30 s at a temperature maximally up to the boiling point of the oil phase to dissolve the suspended carotenoid in said oil phase and obtain a heated oily carotenoid solution;
- iii) cooling the heated oily carotenoid solution by methods selected from the group consisting of mixing with a physiological acceptable oil phase that is at a lower temperature than the heated oily solution and using a heat exchanger.
- iv) adding the cooled oily carotenoid solution to highly porous inorganic carriers; and
- v) adding the carriers to nutritional compositions.

The disclosure further describes an oily carotenoid suspension of astaxanthin particles, wherein the astaxanthin complies with the following quality criteria and specifications:

| Quality Criteria | Specification |
| --- | --- |
| Physical State | Solid |
| 0.05% Solution in Chloroform | Complete and Clear |
| Absorption Maximum Wavelength | 484-493 nm (solution in chloroform) |
| Residue on Ignition | Not more than 0.1% |
| Total Carotenoid Content other than Astaxanthin | Not more than 4% |
| Lead | Not more than 5 ppm |
| Arsenic | Not more than 2 ppm |
| Mercury | Not more than 1 ppm |
| Heavy Metals | Not more than 10 ppm |
| Assay | Minimum 96% |

The disclosure further describes an oily carotenoid suspension of canthaxanthin particles, wherein the cantaxanthin complies with the following quality criteria and specifications:

| Quality Criteria | Specification |
| --- | --- |
| Physical State | Solid |
| 1% Solution in Chloroform | Complete and Clear |
| Melting Range (decomposition) | 207-212° C. (corrected) |
| Loss on Drying | Not more than 0.2% |
| Residue on Ignition | Not more than 0.2% |
| Total Carotenoid Content other than trans-canthaxanthin | Not more than 5% |
| Lead | Not more than 10 ppm |
| Arsenic | Not more than 3 ppm |
| Mercury | Not more than 1 ppm |
| Assay | Minimum 96 to 101% |

In a further exemplary embodiment of the disclosure the oil phase added to cool the oily carotenoid solution may contain up to 30% of emulsified water.

The aforementioned astaxanthin and canthaxanthin oily suspensions meeting US-FDA requirements are also particularly suitable for preparation of water dispersible formulations as described in U.S. Pat. No. 5,364,563 and U.S. Pat. No. 6,664,300.

According to exemplary embodiments, the oily carotenoid solution is added to a nutritional composition inline or batchwise after cooling and the nutritional compositions are selected from the group consisting of feed pellets, granulates, tablets and capsules etc. The oily solution thus obtained gives more consistent distribution of molecularly dispersed carotenoid in the oil in feed pellets and other nutritional compositions.

Furthermore the oily carotenoid solution may be added to highly porous powder with large internal surfaces, which are further processed with nutritional compositions, e.g., with feed compositions, or can be used on their own and processed into tablets, capsules etc. for oral, pharmaceutical or nutriceutical administration.

In the description of the following disclosure, the definitions and terms have the following preferred meanings:

"Excipients" are materials with no pharmacological activity in the amounts employed and may be included in compositions to improve technical handling e.g. solubility and stability of carotenoids and facilitate administration to a living organism.

"Dissolving" or "dissolution" means obtaining molecular dispersions or molecular aggregates of a carotenoid which may be monomers, dimers, trimers etc and/or colloidal dispersions of the carotenoid. Assessment of the degree of dissolution of the carotenoid in an oily phase is performed by filtration of the oily phase through a 0.45 μm pore size filter, followed by HPLC determination of the carotenoid content in the filtrate and compared with the total carotenoid concentration in the unfiltered oily phase. "Substantially" means at least 40 wt %.

"Formulated carotenoid" refers to colloid-dispersed compositions comprising a carotenoid with excipients such as protective hydrocolloids or polymeric dispersants and stabilisers and includes powdered cells and cell fragments e.g., microalgae such as *H. pluvialis, Chlorococcum* and *Phaffia rhodozyma*.

"Feed" covers all types of food fed to living species.

"Fish-feed" describes all feed compositions comprising proteins, carbohydrates, oils, minerals, vitamins and nutrients, etc., used in aquaculture for feeding fish particularly salmonids and crustaceans.

"Crystalline carotenoid" describes crystal structures of the compound which include defined polymorphs and pseudo polymorphs "In-line" refers to a method or process which constitutes an integral part of a continuous sequence of operations or steps.

Carotenoids are a class of hydrocarbons consisting of eight isoprenoid units. The carotenoid class of compounds is classified into two main groups: carotenes and xanthophylls. In contrast to carotenes, which are pure polyene hydrocarbons, such as beta-carotene or lycopene, xanthophylls additionally contain functional moieties such as hydroxyls, epoxy and/or oxo groups. Typical representatives of this group are astaxanthin, canthaxanthin and zeaxanthin.

Xanthophylls are very common in nature and occur in corn (zeaxanthin), in green beans (lutein), in paprika (capsanthin), in egg yolk (lutein) and also in crustaceans and salmon (astaxanthin). They impart their characteristic colour to these foods.

Some carotenoids may be synthesized industrially or may be isolated from natural sources. They are important natural antioxidants and colourants for the food and feed industries and for the pharmaceutical industry as a substitute for synthetic dyes.

Xanthophylls are, at ambient conditions practically insoluble in water and show very low solubility in fats and oils. It is claimed in the prior art that the limited solubility and the high sensitivity to oxidation prevent direct use of the crystalline material obtained from synthesis in colouring foods and feeds.

Preferred carotenoids are astaxanthin and canthaxanthin or mixtures thereof used in the fish feed industry. For applications in other food and feed industries alternative carotenoids such as β-carotene, lycopene, bixin, zeaxanthin, cryptoxanthin, lutein, βapo-8' carotenal, β-apo-12' carotenal as well as esters and derivatives may be considered. Fatty acid esters and diesters of astaxanthin and canthaxanthin which are more oil-soluble may be used in place of the free carotenoid base. Preferred examples are the diesters of astaxanthin prepared with an omega-3 fatty acid and/or a short chain carboxylic acid which are described in U.S. Pat. No. 6,709,688 and incorporated herewith as reference.

The carotenoid may be amorphous, in the form of H- or J-aggregates or present in a stable or metastable polymorph. Qualities of astaxanthin and canthaxanthin suitable for the disclosure are described in the US-FDA data base (21CFR73.35 and 21CFR73.75) incorporated herein by reference. Also substantially pure carotenoids can be used with the proviso that the by-products are identified, or belong to the class of carotenoids present in food and feed compositions suitable for consumption and are known to be harmless.

Pure compounds or mixtures of astaxanthin and canthaxanthin and their polymorphs amorphous and aggregate forms comprising up to 40% by weight of functional all trans-carotenoids may be used. The astaxanthin may contain 60%-98%, preferably 80% to 96% of trans-astaxanthin and between 2% to 40% by weight, preferably 2% to 35%, most preferably 2% to 4%, parts by weight of at least one carotenoid derivative as minor component/s in the combination.

It should be understood that formulated carotenoid compositions and astaxanthin from natural sources comprising powdered cells and cell fragments e.g., microalgae such as *H. pluvialis* and *Chlorococcum*. Yeast, such as *Phaffia rhodozyma* and crustacean by-products may be used as a source of astaxanthin in the production of fish feed according to this disclosure. The method described enables higher, more consistent and uniform dissolution of the carotenoid from (freeze or spray) dried cell components, for incorporating into fish feed thereby resulting in a more homogeneous product. Furthermore, using an in-line process for dissolving astaxanthin in an oil phase and for production of fish pellet is a much more cost efficient and industrially viable method for preparing high quality feed with improved properties.

For in-line dissolution according to the method described in the present disclosure, the oil composition comprises 0.1% to 40% by weight of suspended astaxanthin. 90% of said particles should have a diameter less than 15 μm. The average particle size of the carotenoid powder suspended in the oil phase should be less than 15 μm, preferably between 1 μm to 5 μm for more rapid dissolution at lower temperatures. Particle sizes smaller then 1 μm may be even more suitable for rapid dissolution in oil. If more soluble polymorphs or amorphous modifications of the carotenoids are used the particle size may be larger. Particle size reduction may be carried out in a colloid ball mill, e.g., by milling a suspension in an oil phase. An alternative, but nonetheless feasible option is to obtain micronised carotenoid is to mill, e.g using a colloid mill, an aqueous suspension of carotenoid comprising a suitable wetting agent, e.g phospholipids. Optionally, after removal of the water the dry powder may be further processed by adding excipients to improve powder flow properties and reduce dustiness and added directly to the oil phase and processed according to the disclosure. Other options such as cryo milling and dry milling by air jet mills may also be considered in some instances. Alternatively, submicron amorphous carotenoid particles may be prepared separately by a melt dispersion process using supercritical fluids. If desired, cost notwithstanding, said method may be integrated in-line in the process according to the disclosure. The carotenoid may also be dispersed in a high boiling point non aqueous liquid e.g., a polyol such as glycerol or propylene glycol and milled (micronised) before it is added to the oil phase.

The oil phase in which the carotenoid is dissolved during the heating process is a physiologically acceptable, edible oil and preferably contains antioxidants like alpha tocopherol and ascorbyl palmitate. Tocopherols such as alpha-tocopherol may also be used as the oil phase to dissolve the carotenoid. The oil phase may reach temperatures as high as 180° C.-230° C. High boiling point oils such as vegetable or corn oil, synthetic or partially synthetic triglycerides sold as MIGLYOL™ are preferred. The oil phase used for the heating process may be either vegetable or fish or a blend of the two oil types. Examples of suitable vegetable oils are: cottonseed oil, sesame oil, coconut oil or peanut oil, almond oil, corn oil, canola oil (rapeseed oil), olive oil, peanut oil (groundnut oil), sunflower oil, safflower oil, vegetable soybean oil, almond oil, apricot kernel, avocado oil, jojoba oil, orange oil, lemon oil, palm kernel oil, pumpkin seed oil, castor oil, coconut oil (76 and 110 degrees), sesame oil, toasted sesame oil, flax seed oil (organic, conventional and high lignan), GLA oils (Borage, Black Currant, Evening Primrose), grapeseed oil, hazelnut oil, kukui nut oil, macademia nut oil, mamaku oil, pecan oil, perilla oil, pistachio oil, rice bran oil, tea tree oil, walnut oil, wheat Germ oil, corn oil or canola oil (rapeseed oil). Preferred vegetable oils are: soya bean oil (GMO free) and linseed oil.

Wherever possible, the process is performed without applying external pressure. Typically pressures up to 50 bar may be generated internally using hydraulic and fluid pressures induced by pump actions in the tubings. But if desired, the pressure may be further increased to about 300 bar to accelerate the dissolution of the carotenoid.

Preferably the oil phase does not contain water. However in some cases, the oil phase used to heat the carotenoid solution and/or the oil phase in which the carotenoid is dispersed may contain a smaller amount, up to ca. 10-30% of emulsified water (waterin-oil emulsion). The presence of an immiscible phase with a lower boiling point compared to the oil phase can generate sufficient superheated steam under pressure to accelerate the dissolution of the carotenoid in the heating zone thus enabling the use of higher carotenoid concentrations. Equally, the oil phase in which the carotenoid is dissolved may be admixed with pressurised (supercritical) fluids e.g, $CO_2$ which may partially mix with or dissolve in the oil phase and enable higher solvency by lowering the melting point of the suspended cartenoid. Cost and economic factors are the main considerations to take into account along with safety issues in the installation and use of high pressure equipment and components. The amount of heated oil phase (at a temperature between 80° C. to 230° C.) for heating and dissolution is in the range of 0.1 to 25 parts, preferably 5 to 10 parts by weight of the carotenoid oil suspension.

The process or parts of the in-line process may be carried out under an inert gas or under pressure in the heating zone to further minimise oxidative degradation. The use of supercritical fluids, e.g., $CO_2$ causes a significant reduction in the melting point of the carotenoid. The inert gas which can be a superheated gas or a pressurised (supercritical) fluid may also be used to increase the pressure in the heating zone thus enabling the carotenoid to dissolve more rapidly at lower temperatures and increasing its dissolution at higher concentrations. The gas phase may also be superheated steam generated from minor amounts of water emulsified in the heated oil phase kept under increased pressures during passage through the heating zone.

The bulk of the oil for cooling and/or diluting the hot solution down to below 60° C. is kept at 30° C.-60° C. or less. It is preferably free of water. However, it may contain a minor proportion of water or water which is naturally present in e.g. crude natural (fish) oils. The amount of water in the oil may be as much as 10-30% by weight or more. It is a minor amount compared to the larger amount of oil employed and essentially it is in a w/o system and not an aqueous solution of an emulsifier. The oil used can be a natural oil or partially hydrolysed natural vegetable or fish triglyceride comprising mono, di-glycerides and triglycerides or combinations thereof that are more easily absorbed. It may also be a synthetic or semi-synthetic oil. Examples of suitable fish oils are: specialty marine oils like Norwegian Cod Liver oil (3000A/100D, 2500A/250D) with omega 3-acids—30% (18% EPA/12% DHA), 50% (30% EPA/20% DHA)-, cholesterol-free, high-potency DHA, fish oil of tuna or bonito, fish liver oil, halibut liver oil, pollack liver oil, shark liver oil, squalene, squalane, salmon oil, skipjack liver oil, herring oil, capelin oil, menhaden fish oil.

Preferably it is fish oil such as those available from Egersund Sildoljefabrikk under the trade names NorseECOil and NORSlamOil or fish and vegetable oil blends from other fish oil producers.

The amount of carotenoid in the resulting oil solution exiting the heat exchanger after cooling or addition of oil phase at a lower temperature is between about 50 ppm to 20,000 ppm, preferably between about 100 ppm to 5,000 ppm, more preferably between about 200 to 1000 ppm. Accordingly the amount of oil phase for cooling the heated carotenoid solution will depend on factors such as the carotenoid, the oil phase and temperature used for dissolution, the desired final concentration of carotenoid in the cooled solution.

The oily solution, as obtained by the method according to the method of the disclosure may be collected in storage vessels to prepare feed or food compositions. In an exemplary embodiment the dissolution apparatus described which forms another aspect of the disclosure is integrated into fish feed production lines. Where the carotenoid is astaxanthin, the temperature and heating conditions are adjusted so that preferably the trans to cis-astaxanthin isomer conversion in the solution is below 50% of total isomers, preferably below 30%. Possible formation of additional by-products such as astacene, semi-astacene and the C-25 aldehyde should be below 10%, preferably below 5% by weight of total astaxanthin.

The amount of oily carotenoid solution comprising astaxanthin added to the feed composition may be in the range of 1-50% by weight. Preferably the amount of oily solution added is between 10 and 30% by weight. The amount of carotenoid dissolved in this oily solution may be from 10 ppm to 300 ppm, preferably between 30 ppm to 100 ppm.

The process of instant disclosure does not require the use of cold water dispersible formulations in the production of nutritional compositions and feed. The production is streamlined and facilitates in-line control over the amount of astaxanthin dissolved in the oil phase. Furthermore the process enables the monitoring of astaxanthin chemically and physically before adding to feed pellets. It avoids complicating enzymatic pre-treatments of the cold water dispersible formulations to liberate astaxanthin from the formulations according to EP0839004.

The oil solution containing the carotenoid may be added directly to colour fat based foods (e.g. margarine in combination with beta carotene) or added to poultry or fish feed compositions: The final cooled oil solution may be emulsified with water prior to addition to the feed to facilitate granulation, extrusion or pelletisation. The water may be removed during further processing or drying of the fish feed. The addition of the oily solution to fish feed may be pre, post or during extrusion of solid feed composition, using reduced, atmospheric or increased pressure. The oily composition may also be optionally filtered before adding to feed pellets to remove undissolved material. Alternatively, the oily carotenoid solution may be processed into solid compositions by addition to highly porous inorganic matrix and carriers, taking advantage of the property of some carriers to absorb oil up to five times their own weight without loosing powder characteristics. Examples of highly porous (100-500 $m^2/g$) inorganic carriers are Zeopharm® and Neusilin®. The resulting particulate solid compositions may be added to feed or food components and processed into suitable administration forms. They may also be used in their own right as oral pharmaceutical and nutriceutical compositions. Preferred highly porous inorganic carriers which are employed in this disclosure include inorganic compounds, e.g. calcium hydrogen phosphate and magnesium aluminometasilicate known under the Trade Marks Fujicalin® types SG and S and Neusilin™, respectively. Typical parameters for Fujicalin® types SG and S include a mean pore size of 7 nm, a mean particle size of about 110 μm, a specific volume of about 2 ml/g, a BET specific surface area of 30 $m^2/g$ to 40 $m^2/g$, and an oil and water absorption capacity of about 0.8 ml/g. Neusilin™ is sold as Grades S1, SG1, UFL2, US2, FH2, FL1, FL2, S2, SG2, NFL2N and NS2N. Especially preferred grades are S1, SG1 US2 and UFL2. The most preferred support material for many applications is grade US2. Other suitable support materials are Zeopharm® 600 (precipitated amorphous calcium silicate) with 300 $m^2/g$, and oil absorption capacity of at least 450 ml/100 g, Hubersorb® 250 NF (precipitated amorphous calcium silicate) with oil absorbing capacity of 250-300 ml/100 g and Zeopharm® 80 (precipitated amorphous silica) with 140 $m^2/g$ and oil absorption capacity of 185-215 ml/100 g. Those materials, which are amorphous, typically have a specific area of about 100 $m^2/g$ to about 300 $m^2/g$, an oil absorption capacity of about 1.3 ml/g to about 4.5 ml/g, a mean particle size of from about 1 μm to about 14 μm and a specific volume of about 2.1 ml/g to about 12 ml/g. However, alternative organic or inorganic porous materials may also be used, as long as they have no deleterious effect on the carotenoid and present internal surface areas which are comparably large. The amount of support material used depends on the specific surface area available for sequestering a solution or dispersion of the carotenoid inside the channels and the properties such as viscosity of the solution employed.

The disclosure does not preclude optionally using colloid-dispersed formulated carotenoids such as granules and beadlets rather than the preferred, unformulated particulate crystalline or amorphous carotenoid compound to prepare the oily carotenoid composition. While the method is described for processing carotenoids, especially astaxanthin and canthaxanthin, zeaxanthin and beta-carotene, a skilled person should be able to apply the disclosed process to other compounds, which may be used together with the carotenoids, having similar physical and chemical properties with only routine changes in processing conditions for adding to nutritional compositions. Examples are functional lipophilic compounds such as sitosterol, sitostanol and their derivatives, coenzyme Q10 and compounds such as fat-soluble vitamins, especially vitamin A and its derivatives.

The method allows the convenient processing of carotenoids either individually or in combination. For example astaxanthin and canthaxanthin can be processed together. Optionally, one or a combination of components or excipients to facilitate processing may be added, said optional components and excipients comprising stabilisers, high boiling point oils and waxes, dispersant aids, polymers, protective colloids, preservatives, flow-aids, membrane lipids, cationic, anionic or non-ionic surfactants.

The carotenoid may be physically admixed with excipients for improving powder flow before it is added to the oil.

It should be understood that the method according to the disclosure is a novel continuous method for preparing a solution of at least one carotenoid in an oil phase by means of an in-line or batch wise process. The method described is not limited to using unformulated, substantially pure crystalline compounds. Colloid-dispersed formulations prepared according to e.g. U.S. Pat. No. 5,364,563, U.S. Pat. No. 6,296,877, and WO 03/102116 cited herein by reference may also be employed.

Method

The method will be described with reference to a flow-chart schematically illustrated in FIG. 1 suitable for carrying out the process in accordance with the disclosure. The process does not normally require to be carried out under pressurised conditions but higher pressures may be generated if a pressurised (supercritical) fluid e.g., $CO_2$ is used with the oil phase or there is a minor amount of water in the oil phase. The layout and configuration of the in-line heating and cooling chambers, heat exchangers, conduits and containing vessels, high pressure components, pressure-relief valves and temperature sensors, etc., appropriately sited at the entrance and exit from the heating zone may be arranged to provide the most suitable integration into established or new feed production lines.

A suspension of at least one carotenoid with average particle size diameter between 1-5 μm, in the selected oil phase or suitable fluid medium, at a concentration of from about 0.1% to 40% by weight based on the mixture, with or without addition of stabilizers, is initially introduced into a vessel 4. A vessel 1 contains high boiling point oil, without suspended carotenoid. The carotenoid suspension may be prepared by suspending a particulate carotenoid or a carotenoid composition and milling it in-line for either containment in the vessel 4 or direct injection into a mixing chamber 6. The carotenoid suspension may also be previously prepared separately on large scale and stored for months before subsequent dissolution according to the method of the disclosure.

In one exemplary embodiment, the oil phase from the vessel 1 is fed by means of a pump 2 after passing the stream through a heat exchanger 3 where it is heated to a temperature at or below its boiling point into a mixing chamber 6. The oil stream in the system may be brought up to the desired temperature, pressure and other operating conditions such as flow rate by purging and equilibrating with recycled oil. A carotenoid suspension which is kept below 100° C. in the vessel 4 is mixed with the heated oil stream in a mixing chamber 6 either at right angles or tangentially via pump 5. Compressed gas may also be used to pump the suspension. The mixing ratio in the heating zone is predeterminable by adjusting the delivery rate of the pump 2, having regard to the oil, target temperature, to be achieved after passage through the mixing chamber 6, in the desired residence time. Dissolution of carotenoid in the heated oil phase occurs at or below the boiling point of the oil which may be from 50° C. to 300° C. The contact time for dissolution may be prolonged by increasing the residence time in the heating zone. This is done by either decreasing the flow rate of the mixing pump 5 or extending the length of the heating conduit 7 (optionally thermostatically controlled or insulated) in order to maintain the desired temperature during transit through the heating zone. The heating zone illustrated in FIG. 1 consists of the mixing chamber 6 and the insulated conduit 7. The residence time in the heating zone during which the desired temperature is maintained may be up to 30 s.

Alternatively, the dimension of the mixing chamber 6 is such that it effectively forms the entire heating zone and at the chosen delivery rate of pump 2, the residence time of the suspension inside the mixing chamber or chamber can be up to 30 s, preferably less than 5 s.

The transit time along the heating zone during which mixing and dissolution takes place is preferably between 0.1 to 30 s when the temperature of the oil phase is between 50° C. to 230° C., preferably between 0.1 to 10 s at temperatures between 100° C. to 230° C. According to an exemplary embodiment the carotenoid is dissolved as rapidly as possible in the oil phase for between 1 to 5 s at temperatures between 120° C. to 180° C., optionally under pressure, thereby minimising degradation and isomerisation to achieve the target carotenoid concentration. It may be acceptable to substantially dissolve the carotenoid particles so that when the oil solution exits at a temperature below 60° C. after processing, the amount of carotenoid in solution is at least 50% by weight of the total carotenoid content in the oil.

To minimise isomerisation, the heating step may be carried out progressively or in stages. Where the stability of the carotenoid is not compromised, the carotenoid suspension may be pre-heated in a vessel before passage through the heating zone. Inside the heating zone the suspension is heated to temperatures below the melting point of the carotenoid for up to 10 s preferably up to 5 s, preferably by mixing with heated oil phase between 80° C. to 120° C. The suspension is then briefly heated along a further section in which the temperature may be above the melting point of the carotenoid or even the boiling point of the oil phase, between 120° C. to 300° C. for less than 5 s. Preferably the suspension is heated briefly at 120° C.-180° C. for 0.1 to 2 s. The transient heating may be described as 'flash-heating'.

Dissolution in the oil phase may also be carried out more effectively at lower temperatures by integration or concurrent use of superheated (supercritical) critical gases and/or a high energy homogeniser selected from the type of mixers such as in-line rotor-stator dispersator, ultra-sonic disintegrator and high-pressure homogeniser including but not limited to microfluidiser. The object is to disintegrate and dissolve the suspended carotenoid as rapidly and briefly as possible at temperatures near or above its melting point with minimum degradation and isomerisation. The carotenoid suspension may also be heated, without dilution or adding a heated oil phase in a mixing chamber by pumping the oil suspension through a heat exchanger where it is heated briefly and rapidly at temperatures which may be even above the boiling point of the oil phase. Application of energy to dissolve the carotenoid may be carried out directly utilising heat exchanger heated by electricity, or heated indirectly by means of a medium including but not limited to super heated steam or heated super critical gases under pressure.

After passage through the heating zone the hot oil solution is immediately cooled inline in less then 30 s in a mixing chamber referred to as a cooling chamber 10 to below about 60° C., or lower temperatures, by adding cooled oil phase, or oil phase at ambient temperatures, via a pump 9 from an oil phase vessel 8 which is kept at a lower temperature than the temperature of the heated carotenoid solution. Preferably cooling is carried out in less than 30 s. The conduit exiting the cooling chamber 10 may be additionally cooled or refrigerated with a heat exchanger using an external medium e.g. water, liquid nitrogen or a compressed gas, particularly if the amount of oil phase added for cooling is not sufficient to bring the temperature of the diluted oil phase solution to below 60° C. The amount of oil phase added for cooling is from 1 to 500 parts by weight of the heated carotenoid solution, preferably 2 to 50 parts depending on the method of cooling and the target concentration of carotenoid in the final solution. The temperature of the carotenoid oil solution after cooling is below 60° C., preferably between 30° to 50° C., more preferably below 30° C.

The hot oil solution exiting from the heating zone may also be cooled immediately by adding it under rigorous agitation to a vessel containing a measured amount of oil phase kept below 60° C., or lower, in a containment vessel for batch-wise preparation. The vessel may be further cooled cryostatically. In any event cooling should be carried out in a short period, preferably less than 30 s.

Appropriate in-line monitoring facilities such as gauges and gate valves which control temperature, pressure, flow rates and direction may be installed in the circuit to control the heating and cooling sequence. The configuration in FIG. 1 is a typical example to illustrate the disclosure. Different configurations and arrangements of the components and their design are possible within the scope of the disclosure.

A dissolution module comprising mixing chambers and heat exchangers for heating and cooling may be adapted for preparing a desired amount of a carotenoid oil solution at a concentration between 50 ppm and 20,000 ppm. The throughput may be scaled up or down by selecting the appropriate design and dimensions of the mixing chambers, orifice diameter and pressure in relation to the required flow rate of the α-rotenoid oil suspension and capacity of the heat exchangers. Mixing chambers using static mixers or mixing nozzles (such as orifice nozzles) may be used. The design of the heat exchanger for heating the oil phase to between 50° to 300° C. in the mixing chamber takes into consideration the void volume and surface area of the heating surface, the suspension throughput, temperature and pressure and the type of heat transfer media employed. A dissolution module powered by a heat exchanger with a energy consumption of 1 kW may be employed to prepare at least 60-180 l/h of a carotenoid oil solution containing 250 ppm of astaxanthin for addition to fish feed either batch wise from a container or integrated in-line with feed manufacturing processes. The module is scaleable to obtain larger amounts of solution containing higher or lower concentrations of the carotenoid as the case may be.

The following examples demonstrate the disclosure by way of example and not by way of limitation. It may be readily adapted by those skilled in the art to practise alternative embodiments by varying carotenoid concentration, energy source and/or processing temperature and conditions within the scope of the disclosure.

Example 1

100 g of crystals containing 80% (+/−2%) synthetic all trans-astaxanthin with circa 20% by-products comprising cis astaxanthin, C-25 aldehyde astaxanthin, astacine and semiastacine are added to soya oil by using a precision engineered Silverson in-line rotor/stator mixer operating under such conditions that a 3000 ppm astaxanthin concentration is achieved. The in-line mixer is connected to a heat exchanger to heat the oil. In combination with the heat developed by the rotor stator the oil may be heated up to a temperature of 180° C. to 230° C. for 10 s. The resulting oily solution of astaxanthin is immediately mixed with a static mixer (Sulzer A G, Winterthur, C H) with a 10 fold excess of Manhedan fish oil heated at 40° C. The resulting oily solution is assayed for degree of dissolved astaxanthin and used for fish feed production.

Example 2

Figure 1:
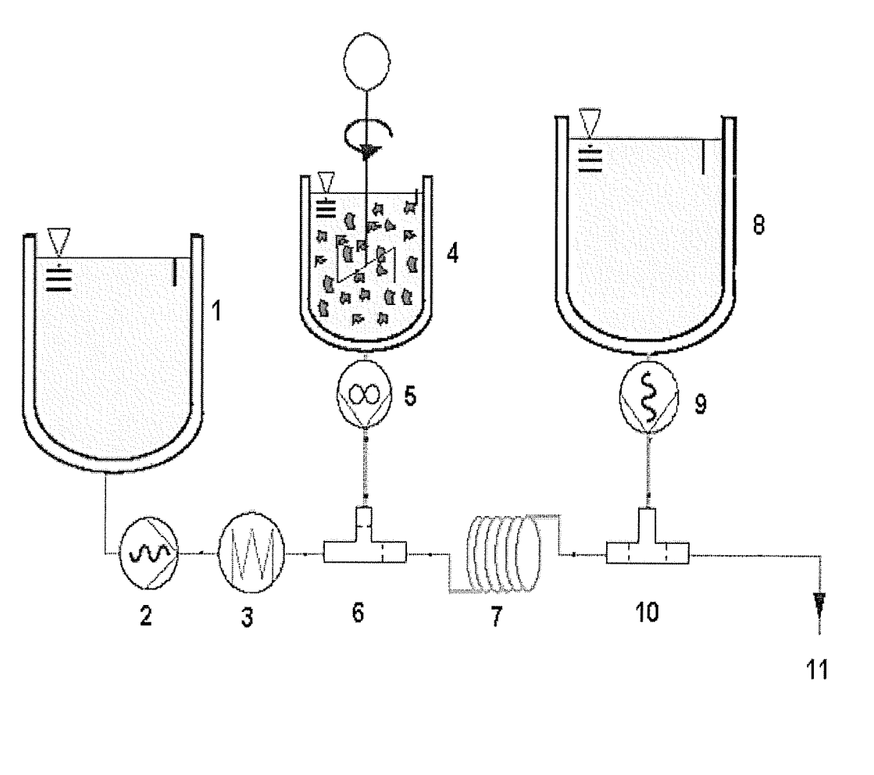
FIG. 1 is a flow chart illustrating an arrangement for in-line heating and mixing followed by cooling with an oil phase at a lower temperature to obtain an oily solution of a carotenoid.

Reference is made to FIG. 1.

Crystalline (98% pure), synthetic, astaxanthin is dispersed using 4% (w/w) in soya bean oil containing 4% (w/w) alpha-tocopherol at room temperature and subjected to a colloidal ball mill procedure performed at 70° C. to achieve a dispersion with the following particle size characteristics (measured with laser diffraction spectroscopy): d10: 1.0 µm, d50: 2.5 µm, d90: 6 µm. The suspension may be prepared separately and stored in a container for preparing an astaxanthin oil solution according to the method of the disclosure.

The suspension is diluted at room temperature with soya bean oil to achieve 1.5% (w/w, 15 000 ppm) astaxanthin and 1.5% alpha-tocopherol. 1 liter of the suspension at 23° C. is transferred to vessel 4 and gently stirred and pumped via mixing pump 5 at 1 kg/h through the mixing chamber 6, in which the astaxanthin suspension is mixed and heated with soy bean oil dosed from vessel 1 via pump 2 operating at 9 kg/h, previously heated to 172° C. by passage through a heat exchanger 3, so that the temperature of the 1:9 (w/w) astaxanthin suspension/pre heated oil mixture at 150° C. contains 1500 ppm astaxanthin. This mixture flows through an insulated tube 7 with a transit time of 1 s (at 150° C.) by applying the flow rate produced by the combined actions of the pump 2 and the mixing pump 5 in conjunction with the volume of the insulated conduit to dissolve the astaxanthin. The solution is immediately mixed and cooled in the cooling chamber 10 with 50 kg/h fish oil kept at 23° C. via pump 9 from the oil vessel 8 to achieve an oily composition of astaxanthin containing 250 ppm astaxanthin which is collected in a container.

Alternatively, the 1:9 (w/w) astaxanthin suspension/pre heated oil mixture (containing 1500 ppm astaxanthin) at 150° C. is cooled without dilution by passage through a heat exchanger, cooled with liquid nitrogen or water, to achieve a 1500 ppm astaxanthin composition having a temperature of 20° C. and collected in a container.

HPLC-analysis of the astaxanthin content after filtration of the 1500 or 250 ppm astaxanthin composition through a 0.45 µm pore size filter shows that the astaxanthin was completely solubilised and contains 75% all trans-astaxanthin and 25% cis isomers and no further degradation products. The oily astaxanthin solution may be further processed by mixing with fish feed pellets.

Example 3

In a manner analogous to Example 2, substantially pure, crystalline, synthetic, astaxanthin of Example 1 is dispersed using 10% (w/w) in soy bean oil containing 10% (w/w) alpha-tocopherol at room temperature. The suspension is subjected to a grinding in a colloid ball-mill at 70° C., to obtain a dispersion with the following particle size characteristics: 4.9%>5 µm, 95.1% between 2.7 and 1 µm (measured by fractionated filtration, followed by HPLC analysis of the astaxanthin content). The suspension is cooled to room temperature and diluted with soybean oil to achieve 1.5% (w/w) (15'000 ppm) astaxanthin and 1.5% alpha-tocopherol. One liter of the suspension at 23° C. is transferred to the vessel 4 and gently stirred and pumped via the mixing pump 5 at a rate of 1 kg/h through the mixing-chamber 6, wherein the astaxanthin suspension is mixed and heated with hot soy bean oil fed from the vessel 1 using the pump 2 operating at 9 kg/h, previously heated to 148° C. by passage through the heat exchanger 3 so that temperature of the 1:9 (w/w) astaxanthin suspension/pre-heated oil mixture (containing 1500 ppm astaxanthin) 126° C. to dissolve the astaxanthin. This mixture is pumped through an insulated tube for 1 s and mixed and cooled in the cooling chamber 10 with 50 kg/h fish oil of 23° C. from the oil vessel 8 via pump 9 to achieve an oily composition of astaxanthin containing 250 ppm astaxanthin and collected in a container.

HPLC analysis of the astaxanthin content after filtration of the 250 ppm astaxanthin composition through a 0.45 µm pore size filter shows that the astaxanthin is completely solubilised and contains 12% cis-isomers.

The oily astaxanthin solution is further processed by dilution with fish oil to 250 ppm at mixing with fish feed pellets at a 30% oil level by weight to achieve a 83 ppm astaxanthin level in the pellet.

Example 4

In a manner analogous to Example 3, the resulting oily astaxanthin solution stream is fed in-line to an extruder to prepare feed pellets.

Example 5

In a manner analogous to Example 2, crystalline canthaxanthin, which is substantially pure (92.5%) is used in place of astaxanthin.

Example 6

In a manner analogous to Example 2, crystalline, astaxanthin purified from natural sources is used instead of synthetic astaxanthin.

Example 7

In a manner analogues to Example 1 a 10% suspension of *Haematococcus pluvialis* containing 1% astaxanthin is diluted with soy oil to obtain a 3000 ppm astxanthin suspension and further processed using the conditions of Example 1 to obtain an oily carotenoid solution.

Example 8

In place of a *H. Pluvialis* suspension, *Phaffia rhiodozyma* cells or cell fragments comprising astaxanthin may be used, as shown in Example 7.

Example 9

The oily solution of Example 3 containing 250 ppm astaxanthin (1 kg) is added to 200 g magnesium alumino silicate (Neusilin) under stirring. The resulting dry powder (1.2 kg) is added to 2.8 kg fish feed pellet material using dry blending technique. Fish pellets are prepared by dry compaction or extrusion and contain 25% w/wt oil and 63 ppm astaxanthin.

It will be appreciated by those skilled in the art that the present invention can be embodied in other specific forms without departing from the spirit or essential characteristics thereof. The presently disclosed embodiments are therefore considered in all respects to be illustrative and not restricted. The scope of the invention is indicated by the appended claims rather than the foregoing description and all changes that come within the meaning and range and equivalence thereof are intended to be embraced therein.

What is claimed is:

1. A method for preparing an oily carotenoid solution which comprises
    i) Preparing a suspension by dispersing at least one carotenoid in an oil;
    ii) heating the suspension in-line for up to 30 seconds at a temperature maximally up to the boiling point of the oil to dissolve the at least one suspended carotenoid in said oil and obtain a heated oily carotenoid solution; and
    iii) cooling the heated oily carotenoid solution by at least one method selected from the group consisting of (a) mixing with an oil that is at a lower temperature than the heated oily solution and (b) using a heat exchanger to cool the heated oily carotenoid solution without dilution, resulting in a cooled oily carotenoid solution,
    wherein in step ii), the suspension is heated at 100 to 300° C. for less than 5 seconds by diluting with preheated oil.

2. The method according to claim 1, wherein the carotenoid is a crystalline carotenoid compound.

3. The method according to claim 1, wherein the heated oily carotenoid solution is cooled by applying at least one method selected from the group consisting of in-line mixing with an oil which is at a lower temperature than the heated oily carotenoid solution, batch wise mixing with an oil which is at a lower temperature than the heated oily carotenoid solution and using an in-line heat exchanger.

4. The method according to claim 1, wherein the cooled oily carotenoid solution contains up to 20,000 ppm of carotenoid and wherein the cooling of the heated oily carotenoid solution is carried out in-line by the addition of fish oil.

5. The method according to claim 1, wherein the temperature of the oily carotenoid solution after cooling is below 60° C. and the cooling step is performed in a time of less than 30 seconds.

6. The method according to claim 1, wherein the oily carotenoid suspension comprises carotenoid particles which are substantially pure and wherein the carotenoid is selected from the group consisting of synthetic or natural astaxanthin, canthaxanthin, beta carotene and zeaxanthin and wherein 90% of said particles have a diameter less than 15 μm.

7. The method according to claim 1, wherein the oily carotenoid suspension comprises carotenoid particles selected from the group consisting of astaxanthin, canthaxanthin and a combination thereof, said astaxanthin complying with the following quality criteria and specifications:

| Quality Criteria | Specification |
| --- | --- |
| Physical State | Solid |
| 0.05% Solution in Chloroform | Clear |
| Absorption Maximum Wavelength | 484-493 nm (solution in chloroform) |
| Residue on Ignition | Not more than 0.1% |
| Total Carotenoid Content other than Astaxanthin | Not more than 4% |
| Lead | Not more than 5 ppm |
| Arsenic | Not more than 2 ppm |
| Mercury | Not more than 1 ppm |
| Heavy Metals | Not more than 10 ppm | and said canthaxanthin complying with the following quality criteria and specifications:

| Quality Criteria | Specification |
| --- | --- |
| Physical State | Solid |
| 1% Solution in Chloroform | Clear |
| Melting Range | 207-212° C. |
| Loss on Drying | Not more than 0.2% |
| Residue on Ignition | Not more than 0.2% |
| Total Carotenoid Content other than trans-canthaxanthin | Not more than 5% |
| Lead | Not more than 10 ppm |
| Arsenic | Not more than 3 ppm |
| Mercury | Not more than 1 ppm. |

8. A method for preparing nutritional compositions, which comprises preparing an oily carotenoid solution in accordance with the method of claim 1, and adding the oily carotenoid solution to nutritional compositions.

9. The method according to claim 1, wherein the oily carotenoid solution is added to a nutritional composition in-line or batch-wise after cooling.

10. The method according to claim 8, wherein the nutritional composition comprises a material selected from the group consisting of feed pellets, feed granulates, feed tablet and capsules.

11. The method according to claim 9, wherein the nutritional composition comprises a material selected from the group consisting of feed pellets, feed granulates, feed tablet and capsules.

12. The method according to claim 1, wherein the oily carotenoid solution is added to a highly porous inorganic carrier comprising an internal surface area in the range of 100-500 $m^2/g$.

13. The method according to claim 12, wherein the highly porous inorganic carrier comprising an internal surface area in the range of 100-500 $m^2/g$ is added to a nutritional composition comprising a material selected from the group consisting of feed pellets, feed granulates, feed tablet and capsules.

14. The method according to claim 1, wherein the at least one carotenoid is a diester of astaxanthin with an omega-3 fatty acid and/or a carboxylic acid.

15. The method according to claim 1, wherein the at least one carotenoid comprises carotenoid particles selected from the group consisting of astaxanthin, canthaxanthin and a combination thereof.

16. The method according to claim 1, wherein the method is at least partially conducted in a dissolution module comprising a mixing chamber and a heat exchanger for heating or cooling.

17. The method according to claim 1, wherein the method is at least partially conducted in a dissolution module comprising a mixing chamber for mixing the suspension with a high boiling point oil without suspended carotenoid, or a mixing chamber for mixing the heated oily carotenoid solution with an oil that is at a lower temperature than the heated oily carotenoid solution.

18. The method according to claim 1, wherein the method is at least partially conducted in a dissolution module comprising a heat exchanger for heating the suspension or a mixture formed from the suspension, or a heat exchanger for cooling the heated oily carotenoid solution or a mixture formed from the heated oily carotenoid solution.

19. The method according to claim 1, wherein the heated oily carotenoid solution is not emulsified.

20. The method according to claim 1, wherein step ii) is conducted by adding the preheated oil which is free of water, to the suspension.

21. The method according to claim 1, wherein the oil of step iii) does not contain water.

22. The method according to claim 1, wherein in step ii), the preheated oil is free of water, and/or in step iii), the oil for cooling the heated carotenoid solution is free of water.

23. The method according to claim 1, wherein in step ii), the preheated oil is free of water or contains up to 30% water, and/or in step iii), the oil for cooling the heated carotenoid solution is free of water or contains up to 30% water.

24. A method for preparing an oily carotenoid solution, the method comprising:
   i) preparing a suspension by dispersing at least one carotenoid in an oil;
   ii) heating the suspension in-line for up to 30 seconds at a temperature of 100 to 300° C. and maximally up to the boiling point of the oil to dissolve the at least one suspended carotenoid in said oil and obtain a heated oily carotenoid solution, wherein in step ii), the suspension is heated by diluting with a preheated oil; and
   iii) cooling the heated oily carotenoid solution by diluting with an oil that is at a lower temperature than the heated oily carotenoid solution, resulting in a cooled oily carotenoid solution.

25. The method according to claim 24, wherein in step ii), the preheated oil is free of water, and in step iii), the oil for cooling the heated carotenoid solution is free of water, and wherein in step ii), the suspension is heated for less than 5 seconds.

26. The method according to claim 24, wherein in step ii), the preheated oil is free of water or contains up to 30% water, and in step iii), the oil for cooling the heated carotenoid solution is free of water or contains up to 30% water.

27. A method for preparing a nutritional composition, the method comprising preparing an oily carotenoid solution in accordance with the method of claim 25, and adding the oily carotenoid solution to a nutritional composition.

28. The method according to claim 27, wherein the oily carotenoid solution is free of water.

29. The method according to claim 28, wherein the nutritional composition comprises a material selected from the group consisting of a feed pellet, a feed granulate, a feed tablet and a capsule.

30. The method according to claim 1, wherein the preheated oil includes a vegetable oil, a fish oil or a combination thereof.

31. The method according to claim 1, wherein the preheated oil includes soya bean oil, linseed oil or a combination thereof.

32. The method according to claim 24, wherein the preheated oil includes a vegetable oil, a fish oil or a combination thereof.

33. The method according to claim 24, wherein the preheated oil includes soya bean oil, linseed oil or a combination thereof.

* * * * *